US006974583B2

(12) United States Patent
Potin et al.

(10) Patent No.: US 6,974,583 B2
(45) Date of Patent: Dec. 13, 2005

(54) PANTETHINESULPHONIC ACID AND/OR A SALT THEREOF AS A FREE-RADICAL SCAVENGER

(75) Inventors: Anthony Potin, Paris (FR); Philippe Touzan, Paris (FR); Pascale Pelletier, Antony (FR)

(73) Assignee: L'Oreal, Paris (FR)

( * ) Notice: Subject to any disclaimer, the term of this patent is extended or adjusted under 35 U.S.C. 154(b) by 213 days.

(21) Appl. No.: 10/244,666

(22) Filed: Sep. 17, 2002

(65) Prior Publication Data

US 2003/0069191 A1 Apr. 10, 2003

(30) Foreign Application Priority Data

Sep. 17, 2001 (FR) .............................. 01 11993

(51) Int. Cl.[7] .............................. A61K 7/00; A61K 7/42; A61K 7/44; A61K 31/60; A61K 31/185
(52) U.S. Cl. ............................ 424/401; 424/59; 424/60; 424/400; 514/159; 514/578
(58) Field of Search ............................ 424/59, 60, 400, 424/401; 514/159, 578

(56) References Cited

U.S. PATENT DOCUMENTS

| 4,749,719 A | 6/1988 | Maruya et al. |
| 5,601,806 A | 2/1997 | Katsumata et al. |
| 6,419,935 B1 * | 7/2002 | Gueret ........................ 424/401 |

FOREIGN PATENT DOCUMENTS

| DE | 32 44 806 | 6/1983 |
| EP | 524 109 | 7/1992 |
| EP | 518 772 | 11/1993 |
| EP | 518 773 | 11/1993 |
| EP | 895 779 | 6/1998 |
| FR | 2532175 | 8/1983 |
| FR | 2642968 | 9/1993 |
| GB | 2 110 536 | 6/1983 |
| JP | 03-054081 | 7/1981 |
| JP | 08-259420 | 3/1995 |
| JP | 08 259420 | 3/1995 |
| JP | 09-059142 | 8/1995 |
| JP | 09-110645 | 7/1997 |
| WO | WO 99/10318 | 4/1999 |
| WO | WO 99/22707 | 5/1999 |
| WO | WO 99/32077 | 7/1999 |
| WO | WO 00/57840 | 10/2000 |
| WO | WO 01/91715 A2 | 12/2001 |

OTHER PUBLICATIONS

C. Montastier et al; "methodes d'objectivation des effets des agents depigmentants chez l'homme"; J. Med. Esth. et Chir. Derm. vol. XXII, 86; Jun. 1995; pp. 93–103.
J.–B. Galey et al.; "Ethylene formation from methionine as a method to evaluate oxygen free radical scavenging and metal inactivation by cosmetics"; International Journal of Cosmetic Science: vol. 13, pp. 65–78; 1991.
Database Caplus En Ligne; Chemical Abstracts Service, Columbus, Ohio, US; Retrieved from STN Database Accession No. 1197: 4511 XP002203354 & JP 08 259420 A; Oct. 8, 1996.
Database Caplus En Ligne; Chaemical Abstracts Service, Columbus, Ohio, US; Retrieved from STN Database Accession No. 1983: 149594 XP002203355 & JP 03 054081 A; Mar. 8, 1991.

* cited by examiner

Primary Examiner—Shelley A. Dodson

(57) ABSTRACT

Pantethinesulphonic acid and/or a salt thereof as a free-radical scavenger. Prevent or combat the harmful effects of UV and/or pollution on the skin, loss of firmness and/or elasticity of the skin, etc.

17 Claims, No Drawings

PANTETHINESULPHONIC ACID AND/OR A SALT THEREOF AS A FREE-RADICAL SCAVENGER

FIELD OF THE INVENTION

The present invention relates to the use of pantethinesulphonic acid and/or a salt thereof as a free-radical scavenger, especially for preventing or treating the signs of actinic ageing of the skin. The invention also relates to a composition containing pantethinesulphonic acid and/or a salt thereof in combination with a melanogenesis inhibitor and a desquamating agent, and also to the use of this composition for preventing or reducing the formation of pigmentation marks and/or for bleaching or depigmenting the skin.

BACKGROUND OF THE INVENTION

In the course of time, different signs appear on the skin, which are very characteristic of ageing, reflected especially by a change in the structure and function of the skin. This ageing, which is physiological in nature, may be accelerated by environmental factors such as repeated exposure of the skin to sunlight, and especially to ultraviolet A rays, to pollution, in particular either to diesel particulates or to cigarette smoke. The action of the environment on the constituents of the skin (including fibres, cells and enzymes) and on the sebum secreted by the skin leads in particular to the formation of oxygenated free radicals. These radicals cause considerable oxidative damage, especially in cell membranes (e.g., membrane permeability), cell nuclei (e.g., destruction of DNA) and tissues, in particular connective tissue (e.g., degradation of the elastin and collagen fibres). This damage leads especially to a loss of firmness and elasticity of the skin.

It has also been suggested that free radicals might be involved in the process of melanin manufacture leading to pigmentation of the skin.

The mechanism of melanin formation is particularly complex and schematically involves the following main steps:

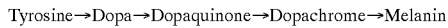

Tyrosine→Dopa→Dopaquinone→Dopachrome→Melanin

Tyrosinase (monophenol dihydroxyl phenylalanine: oxygen oxidoreductase EC 1.14.18.1) is the essential enzyme involved in this sequence of reactions. It especially catalyses the conversion of tyrosine into dopa (dihydroxyphenylalanine) by virtue of its hydroxylase activity. However, certain authors think that the step of hydroxylation of tyrosine to dopa might be initiated by OH. radicals (C. Montastier et al., Méthodes d'objectivation des effets des agents dépigmentants chez l'homme, [Methods for evaluating the effects of depigmenting agents in man], *J. Med. Esth. and Chir. Derm.*, Vol. XXII, 86, June 1995, pp. 93–103), incorporated herein by reference.

The free radicals formed due to the effect of environmental factors thus may lead to an increase in the formation of melanin, and thereby cause or accentuate certain undesirable hyperpigmentations such as idiopathic melasmas, occurring during pregnancy ("pregnancy mask" or chloasma) or during oestro-progestative contraception, or alternatively localized hyperpigmentations, such as senile pigmentation marks known as actinic lentigo. It is thus necessary to protect the skin against these free radicals.

This protective function is normally provided by enzymes present in skin tissue. However, in certain circumstances, the role of these enzymes is insufficient to totally block the destructive action of free radicals.

It has thus been proposed to use various natural and synthetic products as cosmetic active agents for combating the formation of free radicals. Among the agents that may be mentioned are:

- free-radical-scavenging compounds such as vitamin C, vitamin E and derivatives thereof, and also carotenoids;
- compounds which stimulate the enzymes that block free radicals, such as compounds that are rich in phosphorus and trace elements;
- compounds that maintain the integrity of the hydrolipid film, having a self-protective function against free-radical-generating radiation. It is in particular gamma-oryzanol, extracted especially from rice bran oil.

SUMMARY OF THE INVENTION

The inventors have now discovered, surprisingly, that pantethinesulphonic acid and salts thereof have free-radical-scavenging properties making it possible to use, especially in cosmetic compositions, for protecting the skin against the effects of UV and pollution, in particular against light-induced ageing, but also in bleaching or depigmenting compositions.

DETAILED DESCRIPTION OF THE INVENTION

As used herein, the term "pollution" means both "external" pollution due, for example, to diesel particulates, to ozone or to heavy metals, and to "internal" pollution which may especially be due to emissions of solvents from paint, from carpet adhesives, from insulators or from wallpapers (such as toluene, styrene, xylene or benzaldehyde), or to cigarette smoke. Specifically, all these pollutants are capable of directly or indirectly generating free radicals.

Pantethinesulphonic acid and its salts have been described as agents for promoting the regrowth of hair (JP-09 110 645), as agents for bleaching the skin (JP-09 059 142), especially by inhibiting tyrosinase activity (FR-2 532 175), and for increasing cell renewal, in particular in anti-ageing compositions also containing a hydroxy acid (JP-08 259 420). It has also been suggested to use them to inhibit skin irritation (JP-03 054 081). However, to the inventor's knowledge, it has never yet been suggested that pantethinesulphonic acid and/or its salts could have free-radical-scavenging properties.

A first subject of the present invention is thus the cosmetic use of pantethinesulphonic acid and/or a salt thereof in a composition containing a medium, for example a physiologically acceptable medium, as a free-radical scavenger.

A second subject of the present invention is the cosmetic use of pantethinesulphonic acid and/or a salt thereof in a composition containing a physiologically acceptable medium, to prevent or combat the harmful effects of UV and/or pollution on the skin.

A third subject of the present invention is the use of pantethinesulphonic acid and/or a salt thereof to manufacture a preparation for preventing or combating the harmful effects of UV and/or pollution on the skin.

Any alkali metal or alkaline-earth metal salt of pantethinesulphonic acid is suitable for use in the present invention. A preferred salt is the calcium salt of pantethinesulphonic acid.

The composition according to the invention is preferably suitable for topical application to the skin and thus generally comprises a physiologically acceptable medium, i.e. a medium that is compatible with the skin and/or its integuments.

The total amount of pantethinesulphonic acid and its salts in the composition according to the invention depends on the desired effect and can range, for example, from 0.001% to 10% by weight and preferably from 0.01% to 5% by weight relative to the total weight of the composition, including all values and subranges therebetween.

The composition containing pantethinesulphonic acid and/or salts may especially be intended for preventing or treating the signs of ageing of the skin, in particular of light-induced ageing (photoaging) and more particularly the loss of firmness and/or elasticity of the skin.

A subject of the invention is thus also a cosmetic process for treating the loss of firmness and/or elasticity of the skin, comprising the application to the skin of a composition containing, in a physiologically acceptable medium, at least one compound chosen from pantethinesulphonic acid and its salts.

A subject of the invention is also the cosmetic use of pantethinesulphonic acid and/or a salt thereof in a composition containing a physiologically acceptable medium, to prevent or treat the loss of firmness and/or elasticity of the skin.

As a variant, the free-radical-scavenging properties of pantethinesulphonic acid and of its salts may be exploited in a bleaching or depigmenting composition. The reason for this is that pantethinesulphonic acid and its salts complement the preventive action of melanogenesis inhibitors and the exfoliant action of desquamating agents by acting on another component of the pigmentation mechanism. In addition, its anti-inflammatory properties and properties of inhibiting tyrosinase activity also make it an active agent of choice in compositions of this type.

The present invention thus also relates to a composition containing, in a physiologically acceptable medium, pantethinesulphonic acid and/or a physiologically acceptable salt, at least one melanogenesis inhibitor, and at least one desquamating agent.

A subject of the invention is also the cosmetic use of this composition to prevent or reduce the formation of pigmentation marks and/or to bleach or depigment the skin.

Any melanogenesis inhibitor may be used in the composition according to the invention, especially the following compounds: kojic acid; ellagic acid; arbutin and its derivatives such as those described in patent applications EP-895 779 and EP-524 109; hydroquinone; aminophenol derivatives such as those described in patent applications WO 99/10318 and WO 99/32077, and in particular N-cholesteryloxycarbonyl-para-aminophenol and N-ethyloxycarbonyl-para-aminophenol; iminophenol derivatives, in particular those described in patent application WO 99/22707; L-2-oxothiazolidine-4-carboxylic acid or procysteine, and also its salts and esters; ascorbic acid and its derivatives, especially ascorbyl glucoside; and plant extracts, in particular of liquorice, of mulberry and of skullcap, without this list being limiting. Ascorbyl glucoside is preferred for use in the present invention.

The composition defined above preferably contains from 0.001% to 5% by weight of melanogenesis inhibitor relative to the total weight of the composition.

For its part, the desquamating agent may preferably be chosen from: α-hydroxy acids such as citric acid, lactic acid, glycolic acid, mandelic acid, malic acid and tartaric acid; β-hydroxy acids and especially salicylic acid and its derivatives; α-keto acids and β-keto acids; retinoids and in particular retinol and retinyl esters; HMG-CoA reductase inhibitors; and sugar derivatives such as O-octanoyl-6'-β-D-maltose. β-Hydroxy acids are preferred for use in the present invention, in particular salicylic acid and its derivatives, and better still 5-n-octanoylsalicylic acid.

The composition defined above preferably contains from 0.01% to 10% by weight of desquamating agent relative to the total weight of the composition.

As indicated above, the compositions according to the invention are preferably suitable for topical application to the skin. They may be in any presentation form normally used for this type of application, especially in the form of an aqueous or oily solution, an oil-in-water or water-in-oil or multiple emulsion, a silicone emulsion, a microemulsion or nanoemulsion, an aqueous or oily gel or a liquid, pasty or solid anhydrous product.

The compositions may be more or less fluid and may have the appearance of a white or coloured cream, an ointment, a milk, a lotion, a serum, a paste, a mousse or a gel. It may optionally be applied to the skin in the form of an aerosol. It may also be in solid form, and for example in the form of a stick. It may be used as a care product and/or as a skin makeup product.

In a known manner, the composition of the invention may also contain adjuvants that are common in cosmetics and dermatology, such as hydrophilic or lipophilic gelling agents, hydrophilic or lipophilic active agents, preserving agents, antioxidants, solvents, fragrances, fillers, sunscreens, pigments, odour absorbers and dyestuffs. The amounts of these various adjuvants are those conventionally used in the fields under consideration, and for example from 0.01% to 20% relative to the total weight of the composition. Depending on their nature, these adjuvants may be introduced into the fatty phase or into the aqueous phase. These adjuvants and the concentrations thereof should be such that they do not affect the advantageous properties of the pantethinesulphonic acid or its salts.

The compositions according to the invention advantageously contain at least one UVA and/or UVB screening agent chosen from organic screening agents and mineral screening agents.

Examples of organic UVA screening agents that are suitable for use in this invention include:

(1) benzophenone derivatives, benzophenones 3 and 5 being preferred;
(2) triazine derivatives and in particular 2,4-bis{[4-(2-ethylhexyloxy)-2-hydroxy]-phenyl}-6-(4-methoxyphenyl)-1,3,5-triazine available from the company Ciba Geigy under the trade name Tinosorb S and 2,2'-methylenebis[6-(2H-benzotriazol-2-yl)-4-(1,1,3,3-tetramethylbutyl)phenol] available from the company Ciba Geigy under the trade name Tinosorb M;
(3) terephthalylidenedicamphorsulphonic acid or benzene-1,4-bis(3-methylidene-10-camphorsulphonic acid) or an alkali metal, alkaline-earth metal or ammonium salt thereof or a salt thereof with an organic base, which corresponds to formula (I) below:

(I)

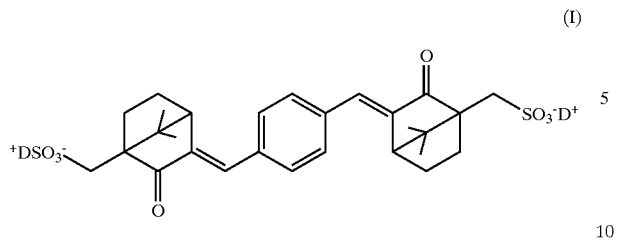

in which D denotes a hydrogen atom, an alkali metal or a radical $NH(R_{25})_3^+$ in which the radicals $R_{25}$, which may be identical or different, denote a hydrogen atom, a $C_1$–$C_4$ alkyl or hydroxyalkyl radical or a group $M^{n+}/n$, $M^{n+}$ denoting a polyvalent metal cation in which n is equal to 2, 3 or 4, $M^{n+}$ preferably denoting a metal cation chosen from $Ca^{2+}$, $Zn^{2+}$, $Mg^{2+}$, $Ba^{2+}$, $Al^{3+}$ and $Zr^{4+}$; and (4) mixtures thereof.

Terephthalylidenedicamphorsulphonic acid is preferred for use in this invention.

Organic UVB screening agents include:
(1) salicylic acid derivatives, in particular homomenthyl salicylate and octyl salicylate;
(2) cinnamic acid derivatives, in particular 2-ethylhexyl p-methoxycinnamate, available from the company Givaudan under the trade name Parsol MCX;
(3) liquid β,β'-diphenylacrylate derivatives, in particular 2-ethylhexyl α-cyano-α,β'-diphenylacrylate, or octocrylene, available from the company BASF under the trade name Uvinul N539;
(4) p-aminobenzoic acid derivatives;
(5) 4-methylbenzylidenecamphor available from the company Merck under the trade name Eusolex 6300;
(6) 2-phenylbenzimidazole-5-sulphonic acid sold under the trade name Eusolex 232 by the company Merck;
(7) 1,3,5-triazine derivatives, in particular:
   2,4,6-tris[p-(2'-ethylhexyl-1'-oxycarbonyl)anilino]-1,3,5-triazine, available from the company BASF under the trade name Uvinul T150, and
   the compound corresponding to the formula (II) below:

(II)

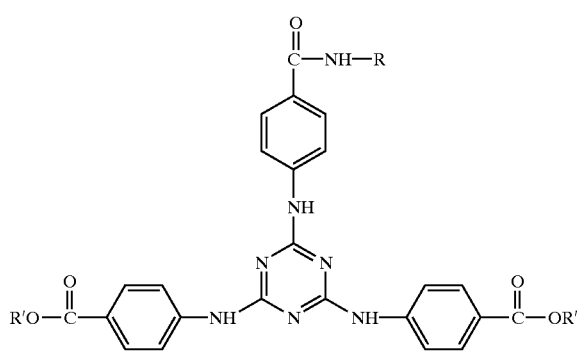

in which R' denotes a 2-ethylhexyl radical and R denotes a tert-butyl radical, available from the company Sigma 3V under the trade name Uvasorb HEB; and
(8) mixtures thereof.

It is preferred to use screening agents (2) and (6).

Useful compounds capable of screening out UVA and UVB radiation (broad band screening agent) include the benzotriazole silicone corresponding to the general formula (III) below:

(III)

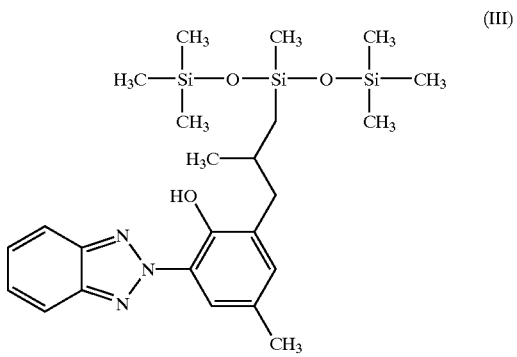

This benzotriazole silicone, and also the method for preparing it, are described in patent application FR-A-2 642 968, incorporated herein by reference.

Mineral screening agents that may be used in the composition according to the invention include nanopigments (mean size of the primary particles: generally between 5 nm and 100 nm and preferably between 10 nm and 50 nm) of coated or uncoated metal oxides such as, for example, nanopigments of titanium oxide (amorphous or crystallized in rutile and/or anatase form), of iron oxide, of zinc oxide, of zirconium oxide or of cerium oxide, which are all UV photoprotective agents that are well known per se. Standard coating agents are, moreover, alumina and/or aluminium stearate. Such coated or uncoated metal oxide nanopigments are described in particular in patent applications EP-A-0 518 772 and EP-A-0 518 773, incorporated herein by reference.

As a variant or in addition, the composition according to the invention containing pantethinesulphonic acid and/or a salt thereof—whether or not it contains a melanogenesis inhibitor and a desquamating agent—may comprise other antipollution agents, whether they are agents capable of trapping free radicals, ozone, aromatic compounds or heavy metals (cobalt, mercury, cadmium and/or nickel).

Antipollution agents that may be used in the composition according to the invention include in particular vitamin C and its derivatives including ascorbyl glucoside; phenols and polyphenols, in particular tannins, ellagic acid and tannic acid; epigallocatechin and natural extracts containing it; extracts of olive tree leaf; extracts of tea, in particular of green tea; extracts of grape marc and of grape seeds; anthocyans; extracts of rosemary; phenol acids, in particular chlorogenic acid; stilbenes, in particular resveratrol; sulphur-containing amino acids such as cysteine; sulphur-containing amino acid derivatives, in particular S-carboxymethylcysteine; ergothioneine; N-acetylcysteine; chelating agents, for instance EDTA, the pentasodium salt or ethylenediaminetetramethylenephosphonic acid, and N,N'-bis(3,4,5-trimethoxybenzyl)ethylenediamine or one of its salts, metal complexes or esters; carotenoids such as crocetin; and various commercial products, for instance the mixture of arginine, histidine ribonucleate, mannitol, adenosine triphosphate, pyridoxine, phenylalanine, tyrosine and hydrolysed RNA, sold by the Laboratoires Sérobiologiques under the trade name CPP LS 2633-12F®, the water-soluble fraction of corn sold by the company Solabia under the trade name Phytovityl®, the mixture of extract of fumitory and of extract of lemon sold under the name Unicotrozon C-49® by the company Induchem, and the mixture of extracts of ginseng, of apple, of peach, of wheat and of barley, sold by the company Provital under the trade name Pronalen Bioprotect®; extracts of water hyacinth or of Eichornia crassipes; phytic acid; chitosan derivatives; vitamin E and its derivatives such as tocopheryl acetate; bioflavonoids; coenzyme Q10 or ubiquinone; certain enzymes, for instance catalase, superoxide dismutase, lactoperoxidase, glutathione peroxidase and quinone reductases; glutathione; benzylidenecamphor; benzylcyclanones; substituted naphthalenones; pidolates; phytanetriol; gamma-oryzanol; lignans; and melatonin.

When the composition according to the invention is an emulsion, the proportion of the fatty phase preferably ranges from 5% to 80% by weight and more preferably from 5% to 50% by weight relative to the total weight of the composition. The fatty substances, the emulsifiers and the co-emulsifiers used in the composition in emulsion form can be chosen from those used conventionally in the field under consideration. The emulsifier and the co-emulsifier are preferably present in the composition in a proportion ranging from 0.3% to 30% by weight and preferably from 0.5% to 20% by weight relative to the total weight of the composition.

As fatty substances that may be used in the invention, it is possible to use oils and especially mineral oils (liquid petroleum jelly), oils of plant origin (avocado oil or soybean oil), oils of animal origin (lanolin), synthetic oils (octyldodecanol), silicone oils (cyclomethicone and dimethicone) and fluoro oils (perfluoropolyethers). Fatty substances that may also be used include fatty alcohols such as cetyl alcohol, fatty acids such as stearic acid, waxes and gums and in particular silicone gums.

Useful emulsifiers and co-emulsifiers that may be used in the invention include, for example, fatty acid esters of polyethylene glycol such as PEG-100 stearate, PEG-50 stearate and PEG-40 stearate; fatty acid esters of polyols, such as glyceryl stearate, sorbitan tristearate and the oxyethylenated sorbitan stearates sold under the trade names Tween® or Tween® 60, for example; sugar esters such as methylglucose sesquistearate and/or its oxyethylenated derivative; and mixtures thereof.

Useful hydrophilic gelling agents that may be mentioned include carboxyvinyl polymers (carbomer), acrylic copolymers such as acrylate/alkylacrylate copolymers, polyacrylamides, polysaccharides, natural gums and clays, and lipophilic gelling agents include modified clays, for instance bentones, metal salts of fatty acids and hydrophobic silica.

The Detailed Description above, in view of the preceding Summary, Background and Field of the Invention, and the Examples to follow, enables one of ordinary skill in the art to make and use the invention as described, and in particular to make and use the following methods, compositions and other preferred embodiments:

Embodiment 1. A method of reducing the effect of free radicals on skin, comprising applying pantethinesulphonic acid, a salt thereof, or a mixture of panthethinesulfonic acid and at least one salt thereof, in an amount effective as a free-radical scavenger to skin in need thereof.

Embodiment 2. A composition comprising a physiologically acceptable medium, pantethinesulphonic acid and/or at least one salt thereof, at least one melanogenesis inhibitor, and at least one desquamating agent.

Embodiment 3. A method for preventing or reducing the formation of pigmentation marks and/or to bleach or depigment the skin, comprising applying the composition of Embodiment 2 in amount effective as a free-radical scavenger to skin in need thereof.

Embodiment 4. A method for preventing or combating the harmful effects of UV and/or pollution on the skin, comprising applying pantethinesulphonic acid, a salt thereof, or a mixture of panthethinesulfonic acid and at least one salt thereof, in amount effective as a free-radical scavenger to skin in need thereof.

Embodiment 5. A method for preventing or treating loss of firmness and/or elasticity of the skin, comprising applying pantethinesulphonic acid, a salt thereof, or a mixture of panthethinesulfonic acid and at least one salt thereof, in amount effective as a free-radical scavenger to skin in need thereof.

Typical areas of the skin in need of reducing the effect of free radicals include the face, neck and hands, where the hands are particularly important for bleaching, and the face is particularly important for other applications.

As noted above, to the inventor's knowledge, it has never yet been suggested that pantethinesulphonic acid and/or its salts could have free-radical-scavenging properties. Thus another aspect of the invention is the packaging, combining, associating, etc., together a) free-radical-scavenging properties and/or the benefits such properties provide on the skin, for example in cosmetic and dermatological usage, with b) pantethinesulphonic acid and/or its salts, for example a composition comprising pantethinesulphonic acid, a salt thereof, or a mixture of panthethinesulfonic acid and at least one salt thereof, in amount effective as a free-radical scavenger. The concept of free-radical-scavenging properties and/or the benefits such properties provide on the skin, for example in cosmetic and dermatological usage, can be indicated in any fashion such as by notation, marking, text, recorded message, etc. This indication can be combined with, associated with, etc. the pantethinesulphonic acid and/or its salts on a package, on or in advertising or on instructions, etc. Such a combination, association, etc. can be termed an "article of manufacture." Clearly, free-radical-scavenging properties and/or the benefits such properties provide on the skin include preventing or combating the harmful effects of UV and/or pollution, and preventing or treating loss of firmness and/or elasticity. In this regard the present application enables one of ordinary skill in the art to make and use the following preferred embodiment:

Embodiment 6. An article of manufacture comprising a) pantethinesulphonic acid, a salt thereof, or a mixture of panthethinesulfonic acid and at least one salt thereof, in combination with b) an indication of free-radical-scavenging properties and/or the benefits such properties provide on the skin, for example in cosmetic and dermatological usage, where the phrase "in combination with" means packaging, combining, associating, etc. as explained above.

The invention will now be illustrated by the non-limiting examples that follow. In these examples, the amounts are indicated as weight percentages.

EXAMPLES

Example 1

Free-radical-scavenging Effect of Calcium Pantethinesulphonate

The free-radical-scavenging effect of calcium pantethinesulphonate was demonstrated by the "ethylene test" based on measurement by gas chromatography of the ethylene formed from the oxidation of methionine by the hydroxyl radical.

The principle of this test is described in the publication "Ethylene Formation from Methionine as a Method to Evaluate Oxygen Free-Radical Scavenging and Metal Inactivation by Cosmetics", J. B. Galey, F. Millecamps and Q. L.

NGuyen, *International Journal of Cosmetic Science*, 13, 65–78 (1991), incorporated herein by reference.

The calcium D-pantethine-S-sulphonate used was obtained from the company Sogo Pharmaceutical Co. in the form of an aqueous solution containing 70% active material.

It was studied in terms of dose effect between 0.1% and 1.5% (w/v of starting material in the reaction medium, i.e. 0.07% to 1.05% w/v of active material).

The results obtained are collated in the following table:

| Concentration of calcium D-pantethine-S-sulphonate (%) | Inhibition of the production of ethylene relative to the control (%) |
|---|---|
| 0.1 | 31.1 |
| 0.5 | 53.6 |
| 1 | 56.6 |
| 1.5 | 61.0 |

The results obtained show that calcium D-pantethine-S-sulphonate has dose-dependent inhibitory power on the production of ethylene. Since this production is proportional to the production of OH. radicals, these results clearly show the free-radical-scavenging effect of this compound.

Example 2

SPF 15 Care Fluid

| | | | |
|---|---|---|---|
| A | Water | | 53% |
| | Glycerol | | 3% |
| | Preserving agents | | 0.5% |
| | Trisodium EDTA | | 0.05% |
| B | Cyclohexasiloxane | | 7% |
| | Glyceryl stearate, PEG-100 stearate, polysorbate 60, cetyl alcohol and stearic acid | | 3.8% |
| | Ethylhexyl methoxycinnamate | | 7.5% |
| | Preserving agents | | 0.15% |
| | Fragrance | | 0.1% |
| C | Water | | 10% |
| | Ammonium polyacryloyldimethyltaurate | | 1% |
| D | Water | qs | 100% |
| | Terephthalylidene dicamphorsulphonic acid | | 0.7% |
| | Phenylbenzimidazolesulphonic acid | | 2% |
| | Triethanolamine | qs pH | 6.5 |
| E | Acrylate copolymer | | 0.3% |
| F | Calcium D-pantethine-S-sulphonate as an aqueous 70% solution | | 1% |

The above composition may be obtained in the following manner.

Phase A is heated with stirring to 80° C. until totally dissolved. Phase B is heated with stirring to 80° C. until a clear phase is obtained and is then added to phase A with stirring. The mixture is then cooled to 60° C. The ammonium polyacryloyldimethyltaurate is swollen at 60° C. in water for 10 minutes and phase C is added to the mixture of phases A+B. Phase D is dissolved with stirring at 50° C. and then added to the mixture of phases A+B+C. The whole is then brought to 30° C. Phases E and F are successively introduced at 30° C. The temperature of the mixture is then brought to 20° C.

This fluid may be used in daily applications to prevent the harmful effects of UV and pollution on the skin.

Example 3

Bleaching Cream

The composition below is prepared in a standard manner for those skilled in the art.

| | |
|---|---|
| Octyldodecanol | 1% |
| Polysorbate 60 | 0.7% |
| Stearic acid | 0.5% |
| Glyceryl stearate and PEG-100 stearate | 1.6% |
| Disodium EDTA | 0.2% |
| Neutralizers | 0.2% |
| Gelling agents | 2.0% |
| Glycerol | 3% |
| Preserving agents | 0.5% |
| 5-n-Octanoylsalicylic acid | 0.1% |
| Cetyl alcohol | 1% |
| Cyclohexasiloxane | 1% |
| Ascorbyl glucoside | 0.05% |
| Calcium pantethinesulphonate as an aqueous 70% solution | 0.1% |
| Water | qs 100% |

This cream may be used in twice-daily applications to bleach the skin and help it regain its transparency.

All reference, texts, patents, applications, standards, documents and product literature mentioned here are incorporated herein by reference, as is French patent application 0111993 filed Sep. 17, 2001, priority to which is expressly claimed.

What is claimed is:

1. A method of reducing the effect of free radicals on skin, comprising applying pantethinesulphonic acid, a salt thereof, or a mixture of pantethinesulfonic acid and at least one salt thereof, in an amount effective as a free-radical scavenger to skin in need thereof.

2. The method according to claim 1, comprising applying on alkali metal or alkaline-earth metal salt of pantethinesulphonic acid to skin in need thereof.

3. The method according to claim 2, wherein the salt of pantethinesulphonic acid is the calcium salt of pantethinesulphonic acid.

4. A composition comprising a physiologically acceptable medium, pantethinesulphonic acid and/or at least one salt thereof, at least one melanogenesis inhibitor, and at least one of salicylic acid or one of its derivatives as a desquamating agent.

5. The composition according to claim 4, wherein the at least one melanogenesis inhibitor is ascorbic acid or one of its derivatives.

6. The composition according to claim 4, wherein the at least one melanogenesis inhibitor is ascorbic acid.

7. The composition according to claim 4, wherein the at least one melanogenesis inhibitor is ascorbyl glucoside.

8. The composition according to claim 4, wherein the desquamating agent is a β-hydroxy acid.

9. The composition according to claim 4, wherein the desquamating agent is salicylic acid.

10. The composition according to claim 4, wherein the desquamating agent is 5-n-octanoylsalicylic acid.

11. The composition according to claim 4, wherein the at least one melanogenesis inhibitor is one or more members selected from the group consisting of ascorbic acid and ascorbyl glucoside and wherein the desquamating agent is selected from the group consisting of salicylic acid and 5-n-octanoylsalicylic acid.

12. The composition according to claim 4, comprising from 0.01% to 5% by weight of the sum of pantethinesulphonic acid and its salts relative to the total weight of the composition.

13. The composition according to claim 4, comprising from 0.001% to 5% by weight of melanogenesis inhibitor relative to the total weight of the composition.

14. The composition according to claim 4, comprising from 0.01% to 10% by weight of desquamating agent relative to the total weight of the composition.

15. The composition according to claim 12, comprising from 0.001% to 5% by weight of melanogenesis inhibitor relative to the total weight of the composition and from 0.01% to 10% by weight of desquamating agent relative to the total weight of the composition.

16. The composition according to claim 4, further comprising at least one UVA and/or UVB screening agent selected from the group consisting of organic screening agents and mineral screening agents.

17. The method according to claim 1, wherein reducing the effect of free radicals on skin further comprises treating signs of ageing of the skin.

* * * * *